US007053100B2

(12) United States Patent
Liotta

(10) Patent No.: US 7,053,100 B2
(45) Date of Patent: *May 30, 2006

(54) THERAPEUTIC NUCLEOSIDES

(75) Inventor: Dennis C. Liotta, McDonough, GA (US)

(73) Assignee: Emory University, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/888,387

(22) Filed: Jul. 9, 2004

(65) Prior Publication Data

US 2004/0242610 A1   Dec. 2, 2004

Related U.S. Application Data

(63) Continuation of application No. 09/007,502, filed on Jan. 15, 1998, now Pat. No. 6,812,233, which is a continuation of application No. 08/451,392, filed on May 26, 1995, now abandoned, which is a continuation of application No. 07/846,303, filed on Mar. 5, 1992, now abandoned, which is a continuation-in-part of application No. 07/776,072, filed on Oct. 11, 1991, now abandoned.

(30) Foreign Application Priority Data

| Mar. 6, 1991 | (GB) | ................................. 9104741.5 |
| May 2, 1991 | (GB) | ................................. 9109505.9 |

(51) Int. Cl.
*A01N 43/54* (2006.01)

(52) U.S. Cl. ...................................... 514/274

(58) Field of Classification Search .................. 514/274
See application file for complete search history.

(56) References Cited

U.S. PATENT DOCUMENTS

| 4,724,232 A | 2/1988 | Rideout et al. |
| 4,874,751 A | 10/1989 | Beacham et al. |
| 5,041,449 A | 8/1991 | Belleau et al. |
| 5,047,407 A | 9/1991 | Belleau et al. |
| 5,059,418 A | 10/1991 | Soike |
| 5,071,983 A | 12/1991 | Koszalka et al. |
| 5,151,426 A | 9/1992 | Belleau et al. |
| 5,204,466 A | 4/1993 | Liotta et al. |
| 5,210,085 A | 5/1993 | Liotta et al. |
| 5,486,520 A | 1/1996 | Belleau et al. |
| 5,538,975 A | 7/1996 | Dionne |
| 5,618,820 A | 4/1997 | Dionne |
| 5,728,575 A | 3/1998 | Liotta et al. |
| 5,814,639 A | 9/1998 | Liotta et al. |
| 5,827,727 A | 10/1998 | Liotta et al. |
| 5,892,025 A | 4/1999 | Liotta et al. |
| 5,914,331 A | 6/1999 | Liotta et al. |
| 5,914,400 A | 6/1999 | Liotta et al. |
| 6,812,233 B1 * | 11/2004 | Liotta ........................ 514/274 |

FOREIGN PATENT DOCUMENTS

| EP | 0 196 185 A2 | 10/1986 |
| EP | 0 206 497 A2 | 12/1986 |
| EP | 0 337 713 A2 | 10/1989 |
| EP | 0 382 519 A2 | 8/1990 |
| EP | 0 382 526 A2 | 8/1990 |
| EP | 0 337 713 A2 | 10/1990 |
| EP | 0 392 791 A1 | 10/1990 |
| EP | 0 494 119 A1 | 7/1992 |
| EP | 0 513 917 A1 | 11/1992 |
| EP | 0 515 144 A1 | 11/1992 |
| EP | 0 515 156 A1 | 11/1992 |
| WO | WO 91/11186 A1 | 8/1991 |
| WO | WO 92/14743 A2 | 9/1992 |
| WO | WO 92/18517 A1 | 10/1993 |

OTHER PUBLICATIONS

*Antiviral Research*, 17(Suppl. 1):1 (3 pages), (Mar. 1992), providing abstracts from the Fifth International Conference on Antiviral Research. Vancouver, B.C., Canada, Mar. 8-13, 1992.

*Virology* (Part 1), 5$^{th}$ International AIDS Congress, Jun. 1989.

Averett, D.R., "Anti-HIV Compound assessment by two novel high capacity assays," *J. Virol. Methods*, 23(3):263-276 (Mar. 1989).

Beach, J. W., et al., "Synthesis of (−)-L-beta-BCH from L-glucose and its anti-HIV and anti-HBV activity," *Abstracts of Papers from the 203$^{rd}$ ACS National Meeting*, 203(1-3), #50 (1992).

Beach, J.W., et al., "Synthesis of Enantiomerically Pure (2'R,5'S)-(-)-1-[2-hydroxymethyl)-oxatiolan-5-yl] Cytosine as a Potent Antiviral Agent Against Hepatitis B Virus (HBV) and Human Immunodeficiency Virus (HIV)," *J. Org. Chem.*, 57:2217-2219 (1992).

Belleau, B., et al., *Chem. Abstr.* 114:43492b (1991).

Choi, W.-B., et al., "Synthesis, Anti-Human Immunodeficiency Virus, and Anti-Hepatitis B Virus Activity of Pyrimidine Oxathiolane Nucleosides," *Bioorgan. and Med. Chem. Lett.*, 3(4):693-696 (1993).

Choi, W.-B., et al, "In Situ Complexation Directs the Stereochemistry of N-Glycosylation in the Synthesis of Oxathiolanyl and Dioxolanyl Nucleoside Analogues," *J. Am. Chem. Soc.*, 113(24):9377-9379 (1991).

Divaker, K., and Reese, C., *J. Chem. Soc., Perkins Trans. I*, 1982:1171 (1982).

Doong, S.-L., et al., "Inhibition of the replication of hepatitis B virus in vitro by 2',3'-thiacytidine and related analogues," *Abstracts of the ICAAC*, p. 181, Abstract No. 496 (Aug. 9, 1991).

(Continued)

Primary Examiner—Alton Pryor
(74) Attorney, Agent, or Firm—Sherry M. Knowles, Esq.; King & Spalding, LLP

(57) ABSTRACT

The use of a 1,3-oxathiolane nucleoside analogue and pharmaceutically acceptable derivatives thereof for the treatment of hepatitis B virus infections is disclosed. Pharmaceutical formulations are also provided.

18 Claims, No Drawings

OTHER PUBLICATIONS

Doong, S.-L., et al., "Inhibition of the Replication of Hepatitis B Virus in vitro by 2',3'-Dideoxy-3'-Thiacytidine and Related Analogues," *Proc. Natl. Acad. Sci. USA*, 88:8495-8499 (Oct. 1991).

Doong, S.-L., et al., *Chem. Abstr.* 115:269987z (1991).

Duschinsky, R., *Nuvleic Acid Chemistry, Part I*, J. Wiley & Sons, New York, 43-46 (1978).

Elion, G.B., et al., "Antagonists of nucleic acid derivatives. VIII. Synergism in combinations of biochemi-cally related antimetabolites," *J. Biol. Chem.*, 208(2):477-488 (Jun. 1954).

Greenberg, S.B., et al., "Metabolism, toxicity and anti-HIV activity of 2'-deoxy-3'-thia-cytidine (BCH-189) in T and B cell lines," *Annals of the New York Academy of Sciences*, 616:517-518 (1990).

Hallongquist, E.G., et al., *Can. J. Research*, 8:129 (1933).

Hesse, G., and Jorder, I., *Chem. Ber.*, 85:924-932 (1952).

Kassianides, C., et al., "Effects of 2',3'-dideoxycytidine on duck hepatitis B virus," *Gastroenterology* 94(5, part 2):A552 (1988).

Liotta, D.C., et al., *Chem. Abstr.* 115:208463d (1991).

Matthes, E., et al., "Potent Inhibition of Hepatitis B Virus Production In Vitro by Modified Pyrimidine Nucleosides," *Antimicrobial Agents and Chemotherapy*, 34(10):1986-1990.

McCollum, R.W., *Viral Hepatitis*, Chapter 12, pp. 327-350.

Miller, R.H., et al., "Common Evolutionary Origin of Hepatitis B Virus and Retrovirus," *Proc. Natl. Acad. Sci. USA*, 83:2531-2535 (1986).

Norbeck, D., et al., "A New 2',3'-Dideoxynucleoside Prototype with In Vitro Activity Against HIV," *Tetrahedron Lett.*, 30(46):6263-6266 (1989).

Robbins, M.J., et al., *Nucleic Acid Chemistry, Part 2*, J. Wiley & Sons, New York, 895-900 (1978).

Schinazi, R.F., et al., *Chem. Abstr.* 115:174631q (1991).

Schleicher and Schuell, S&S, 10 Optical Ave., Keene, NH 03431, Publication No. 700, 1987.

Sells, M.A., et al, "Production of Hepatitis B Virus Particles in Hep G2 Cells Transfected with Cloned Hepatitis B Virus DNA," *Proc. Natl. Acad Sci. USA*, 84:1005-1009 (1987).

Sells, M.A., et al., "Replicative intermediates of hepatitis B virus in HepG2 cells that produce infectious virions," *J. Virol.*, 62(8):2836-2844 (Aug. 1988).

Soike et al., *Chem. Abstr.* 115:174635u (1991).

Soudeyns, H., et al., "Anti-Human Immunodeficiency Virus Type 1 Activity and In Vitro Toxicity of 2'-Deoxy-3'-Thiacytidine (BCH- 189), a Noval Heterocyclic Nucleoside Analog," *Antimicrobial Agents and Chemotherapy*, 35(7): 1386-1390 (Jul. 1991).

Southern, E.M., "Detection of specific sequences among DNA fragments separated by gel electrophore-sis," *J. Mol. Biol.*, 98(3):503-517 (Nov. 5, 1975).

Sung, W.L., "Synthesis of 4-triazolopyrimidinone nucleotide and its application in synthesis of 5-methylcytosine-containing oligodeoxyribonucleotides" *Nucleic Acids Res.*, 9(22):6139-6151 (Nov. 25, 1981).

Tyle, P., *Pharmaceutical Research*, 3(6):318-326 (1986).

* cited by examiner

THERAPEUTIC NUCLEOSIDES

This application claims priority to U.S. patent application Ser. No. 09/007,502 filed Jan. 15, 1998, now U.S. Pat. No. 6,812,233 now allowed, which is a continuation of U.S. patent application Ser. No. 08/451,392, filed May 26, 1995, now abandoned which is a continuation of U.S. patent application Ser. No. 07/846,303, filed Mar. 5, 1992, now abandoned which is a continuation-in-part of U.S. patent application Ser. No. 07/776,072, filed Oct. 11, 1991, now abandoned, which claims priority from GB 9104741.5, filed Mar. 6, 1991 and from GB 9109505.9, filed May 2, 1991.

The present invention relates to the use of a 1-(2-(hydroxymethyl)-1,3-oxathiolan-5-yl)-cytosine derivative and physiologically functional derivatives thereof for the treatment of hepatitis B viral infections.

Hepatitis B virus (HBV) is a viral pathogen of major worldwide importance. HBV is most common in Asian Countries, and prevalent in sub-Saharan Africa. The virus is etiologically associated with primary hepatocellular carcinoma and is thought to cause 80% of the world's liver cancer. In the United States more than ten thousand people are hospitalized for HBV illness each year, an average of 250 die with fulminant disease. The United States currently contains an estimated pool of 500,000–1 million infectious carriers. Chronic active hepatitis will develop in over 25% of carriers and often progresses to cirrhosis. It is estimated that 5000 people die from HBV-related cirrhosis each year in the U.S.A. and that perhaps 1000 die from HBV-related liver cancer. Even when a universal HBV vaccine is in place, the need for effective anti-HBV compounds will continue. The large reservoir of persistently infected carriers, estimated at 220 million worldwide, will receive no benefit from vaccination and will continue at high risk for HBV-induced liver disease. This carrier population serves as the source of infection of susceptible individuals perpetuating the instance of disease particularly in endemic areas or high risk groups such as i.v. drug abusers and homosexuals. Thus, there is a great need for effective antiviral agents, both to control the chronic infection and reduce progression to hepatocellular carcinoma.

Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease as outlined above. In "Viral Infections of Humans" (second edition, Ed. Evans, A. S. (1982) Plenum Publishing Corporation, New York), Chapter 12 describes the etiology of viral hepatitis infections.

European Patent Specification 0 382 526 discloses certain 1,3-oxathio-lane nucleoside analogues which are effective in inhibiting the replication of human immunodeficiency virus (HIV).

Since the priority date of this patent application, the following items have been published: Doong, S. L. et al., Inhibition of the replication of hepatitis B virus in vitro by 2',3'-dideoxy-3'-thiacytidine and related analogs, Proc. Natl. Acad. Sci. USA, 88 (19), 8495–9 (1991); Liotta, D. C. and Choi, W. B., Synthesis of BCH-189 and related compounds, PCT Appl. WO 91/11186; Soudeyns, H. et al., Anti-human immunodeficiency virus type 1 activity and in vitro toxicity of 2'-deoxy-3'-thiacytidine (BCH-189), Antimicrob. Agents Chemother., 35 (7), 1386–90 (1991) and Choi, W. B. et al., In situ complexation directs the stereochemistry of N-glycosylation in the synthesis of thialanyl and dioxolanyl nucleoside analogs, J. Am. Chem. Soc., 113 (24), 9377–9 (1991).

We have now surprisingly found that a 1-(2-(hydroxymethyl)-1,3-oxathiolan-5-yl)-cytosine derivative of formula I

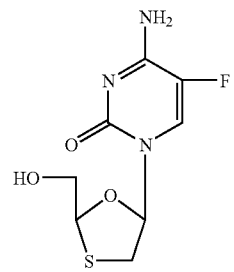

namely 1-(2-(hydroxymethyl)-1,3-oxathiolan-5-yl)-5-fluorocytosine or a pharmaceutically acceptable salt, ester or other physiologically functional derivatives thereof have potent activity against HBV.

It should be noted that the compound of formula (I) contains two chiral centers and therefore exists in the form of two pairs of optical isomers (i.e. enantiomers) and mixtures thereof including racemic mixtures. Thus, the compound of formula (I) may be either a cis or a trans isomer or mixtures thereof. Each cis and trans isomer can exist as one of two enantiomers or mixtures thereof including racemic mixtures. All such isomers and mixtures thereof including racemic mixtures and tautomeric forms of the compound of formula (I) are within the scope of the invention. The cis isomers of the compound of formula (I) are preferred.

According to one feature of the present invention we provide the compound of formula (I) or a physiologically functional derivative thereof for use in the treatment or prophylaxis of a hepatitis B virus infection. According to a further feature of the present invention we provide the use of the compound of formula (I) or a physiologically functional derivative thereof, in the manufacture of a medicament for the treatment or prophylaxis of a hepatitis B virus infection.

In a further aspect of the present invention there is included a method for the treatment or prophylaxis of a hepatitis B virus infection in a host, for example, a mammal such as a human which comprises treating the host with a therapeutically effective amount of the compound of formula (I) or a physiologically functional derivative thereof.

By "physiologically functional derivative" is meant a pharmaceutically acceptable salt, amide, ester or salt of an ester of the compound of formula (I) or any other compound which upon administration to the recipient, is capable of providing (directly or indirectly) the said compound of formula (I) or an active metabolite or residue thereof.

Preferred esters in accordance with the invention include carboxylic acid esters in which the non-carbonyl moiety of the carboxylic acid portion of the ester grouping is selected from straight or branched chain alkyl e.g. n-propyl, t-butyl, n-butyl, alkoxyalkyl (e.g. methoxymethyl), arylalkyl (e.g. benzyl), aryloxyalkyl (e.g. phenoxymethyl), and aryl (e.g. phenyl); sulfonate esters such as alkyl- or arylalkylsulfonyl (e.g. methanesulfonyl); amino acid esters (e.g. L-valyl or L-isoleucyl); dicarboxylic acid esters (e.g. hemisuccinate); and 5'-mono- di- or tri-phosphate esters. The phosphate esters may be further esterified by, for example, a $C_{1-20}$ alcohol or reactive derivative thereof, or by a 2,3-di($C_{6-24}$) acyl glycerol. Any alkyl moiety present in such esters advantageously contains 1 to 18 carbon atoms, particularly 1 to 4 carbon atoms. Any aryl moiety present in such esters advantageously comprises a phenyl group optionally substituted e.g. by halogen, $C_{1-4}$ alkyl, $C_{1-4}$ alkoxy or nitro.

The above-mentioned pharmaceutically acceptable amides of the compound of formula (I) include those derivatives wherein the cytosine amino group is present in the form of an amide, e.g. —NHCOR where R is $C_{1-6}$ alkyl or aryl (e.g. phenyl optionally substituted by halogen, $C_{1-4}$ alkyl, $C_{1-4}$ alkoxy, nitro or hydroxyl).

Examples of pharmaceutically acceptable salts according to the invention include base salts, e.g. derived from an appropriate base, such as alkali metal (e.g. sodium), alkaline earth metal (e.g. magnesium) salts, ammonium and $NX_4^+$ (wherein X is $C_{1-4}$ alkyl). Pharmaceutically acceptable acid addition salts include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

The amount of the compound of formula (I) (hereinafter also referred to as the "active ingredient") or physiologically functional derivative thereof which is required in a medication to achieve the desired effect will depend on a number of factors, in particular the specific application, the nature of the particular compound used, the mode of administration and the condition of the patient. In general a suitable dose will be in the range of 3.0 to 120 mg per kilogram body weight of the recipient per day, preferably in the range of 6 to 90 mg per kilogram body weight per day and most preferably in the range 15 to 60 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally, the active ingredient should be administered to achieve peak plasma concentrations of the active ingredient of from about 1 to about 75 µM, preferably about 2 to 50 µM, most preferably about 3 to about 30 µM. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

In the manufacture of a medicament according to the invention, hereinafter referred to as a "formulation", the compound of formula (I) or a physiologically functional derivative thereof herein as "active ingredient", is typically admixed with, inter alia, one or more pharmaceutically acceptable carriers or excipients and optionally other therapeutic agents.

The formulations include those suitable for oral, rectal, nasal, topical (including transdermal, buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients.

In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example hydroxypropylmethyl cellulose in varying proportions to provide the desired release profile. Tablets may optionally be provided with an enteric coating, to provide release in parts of the gut other than the stomach.

Formulations suitable for oral use as described above may also include buffering agents designed to neutralize stomach acidity. Such buffers may be chosen from a variety of organic or inorganic agents such as weak acids or bases admixed with their conjugated salts.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 35%, preferably about 3% to 15%. As one particular possibility, the active compound may be delivered from the patch by electrotransport or iontophoresis as generally described in *Pharmaceutical Research*, 3 (6), 318 (1986).

Formulations for rectal administration may be presented as a suppository with a suitable base comprising for example cocoa butter or a salicylate.

Formulations suitable for vaginal administration may be presented as pessaries, tampons, creams, gels pastes, foams or spray formulations containing in addition to the active ingredient such carriers as are known in the art to be appropriate.

Formulations suitable for parenteral administration include aqueous and non-aqueous isotonic sterile injections solutions which may contain anti-oxidants, buffers, bacteriostats and solutes which render the formulation isotonic with the blood of the intended recipient; and aqueous and non-aqueous sterile suspensions which may include suspending agents and thickening agents, as liposomes or other microparticulate systems which are designed to target the compounds to blood components or one or more organs. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The compound of formula I may be prepared for example by:

a) reacting an optionally protected 5-F-cytosine compound with a 1,3-oxathiolane of formula (IIA)

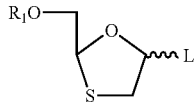
(IIA)

wherein $R_1$ is hydrogen or a hydroxy protecting group and L is a leaving group; or b) reacting a compound of formula (IIB)

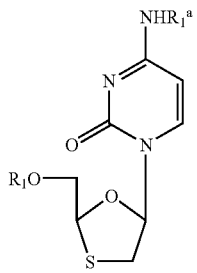
(IIB)

(wherein $R_1$ is as defined above and $R_1^a$ is an amino protecting group) with a fluorinating agent serving to introduce a fluorine atom in the 5-position of the cytosine ring; or c) reacting a compound of formula (IIC)

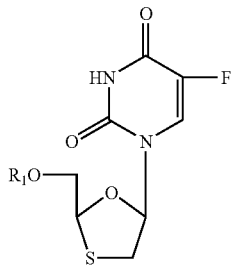
(IIC)

(wherein $R_1$ is as defined above) with an agent serving to convert the oxo group in the 4-position of the uracil ring to an amino group; any remaining protecting groups being removed for example by acid or base hydrolysis to produce the desired product.

With regard to process a), the hydroxy protecting group includes protecting groups such as acyl (e.g. acetyl), arylacyl (e.g. benzoyl or substituted benzoyl), trityl or monomethoxytrityl, benzyl or substituted benzyl, trialkylsilyl (e.g. dimethyl-t-butylsilyl) or diphenylmethylsilyl. The 5-F-cytosine compound may be optionally protected with silyl, e.g. trimethyl silyl groups. Such groups may be removed in conventional manner. The leaving group L is a leaving group typical of those known in the art of nucleoside chemistry e.g. halogen such as chlorine or bromine, alkoxy such as methoxy or ethoxy or acyl such as acetyl or benzoyl.

The reaction in process a) may be effected in an organic solvent (e.g. 1,2-dichloroethane or acetonitrile) in the presence of a Lewis acid such as stannic chloride or trimethylsilyl triflate.

Compounds of formula IIA may be obtained from a suitably protected 2-hydroxyacetaldehyde of formula (III), $$R_1OCH_2CHO \qquad (III)$$

wherein $R_1$ is defined above, as described in Can. J. Research, 8, 129 (1933) and European Patent Specification 0 382 526. Reaction of compounds of formula (III) with a mercaptoacetal $HSCH_2CH(OR)_2$, wherein R is $C_{1-4}$ alkoxy such as $HSCH_2CH(OC_2H_5)_2$, known in the art (Chem. Ber. 85:924–932, 1952), yields compounds of formula IIA wherein L is OR (alkoxy) e.g. methoxy or ethoxy. Alternatively, compounds of formula IIA, wherein L is alkoxy, may be converted to compounds of formula IIA wherein L is halogen or acyl by methods known in the art of carbohydrate chemistry.

Compounds of formula (III) may be prepared from 1,2-0-isopropylidene glycerol by introduction of $R_1$ (e.g. trisubstituted silyl, benzyl or trityl) and removal of the isopropylidene group with mild acid (e.g. aqueous formic or acetic acid) or zinc bromide in acetonitrile, followed by oxidation of the alcohol group with aqueous periodate.

With regard to process b), the 5-fluoro substituent may be introduced by methods known in the art (M. J. Robins, et al., in Nucleic Acid Chemistry, Part 2, L. B. Townsend and R. S. Tipson, editors, J. Wiley and Sons, New York, 895–900 (1978) and references therein; R. Duschinsky in Nucleic Acid Chemistry, Part 1, L. S. Townsend and R. S. Tipson, editors, J. Wiley and Sons, New York, 43–46 (1978) and references therein). The fluorinating agent may be, for example, trimethylhypofluorite in fluorotrichloromethane.

With regard to process c), the compound of formula (IIC) is advantageously treated with 1,2,4-triazole, advantageously together with 4-chlorophenyl dichlorophosphate, to form the corresponding 4-(1,2,4-triazolyl) compound which is then converted to the desired 4-amino (cytidine) compound by reaction with for example methanol.

The starting materials of formula (IIB) and (IIC) may be prepared for example by reaction of an appropriate (optionally protected) base with a compound of formula IIA in an analogous manner to that described in process a) 5-Fluorouracil and 5-fluorocytosine are commercially available from Aldrich Chemical Co., Milwaukee, Wis. 53233, USA.

Separation of the (±)-cis and (±)-trans isomers for example in a protected form, may be accomplished by chromatography on silica gel with mixtures of organic solvents such as ethyl acetate/methanol, ethylacetate/hexane or dichloromethane/methanol. Any protecting group may then be removed using the appropriate reagent for each group.

The compound of formula (I) may be converted into a pharmaceutically acceptable esters and amides by reaction with an appropriate acylating agent, for example, an acid halide or anhydride serving to acylate the 5'-OH and 4-NH$_2$ groups. The acyl group may then be removed selectively from one or other of the 5'-OH and 4-NH$_2$ groups. For, example, treatment of the diacylated compound under acidic conditions, eg. a Lewis acid such as zinc bromide in methanol, removes the 4N-acyl group- to yield the corresponding 5'-OH ester where treatment of the diacylated compound under alkaline conditions, eg. with sodium methoxide removes the 5'-OH acyl group to yield the corresponding 4N-amide. The acyl groups can also be removed selectively by treatment with commercially available esterase or lipase enzymes, eg. pig liver esterase or pancreatic lipase, or by treatment in accordance with methods described in U.S. Pat. No. 5,071,983. The compound of formula (I) may be converted into a pharmaceutically acceptable salt thereof in a conventional manner, for example, by treatment with an appropriate base. An ester or salt of a compound of formula (I) may be converted into the parent compound, for example, by hydrolysis.

For a better understanding of the invention, the following Examples are given by way of illustration.

EXAMPLE 1 cis-1-(2-(Hydroxymethyl)-1,3-oxathiolan-5-yl)-5-fluoro-cytosine

Method A: (±)-cis and (±)-trans 2-benzoyloxymethyl-5-(N$_4$-acetyl-cyto-sin-1-yl)-1,3-oxathiolane are prepared and separated to the ±)-cis and (±) trans isomers as described in European Patent Specification 0 382 526. (See U.S. Pat. No. 5,047,407.) The (±)-cis isomer is fluorinated with trifluoromethyl hypofluorite in fluorotrichloromethane (CCl$_3$F) and chloroform at –78° C., according to the method of Robins, et al. Nucleic Acid Chemistry, Part 2, 895–900, 1978. The N$_4$-acetyl and 2-benzoyl groups are removed with dimethylamine in ethanol, and the product, (±)-cis-1-(2-(hydroxymethyl)-1,3-oxathiolan-5-yl)-5-fluorocytosine, is isolated.

Method B: (±)-cis and (±)-trans-2-benzoyloxymethyl-5-(uracil-1-yl)-1,3-oxathiolane are prepared as described in EP 0 382 526. After deprotection of the 2-hydroxyl group with saturated methanolic ammonia, the isomers are separated on silica gel using EtOAc/MeOH as eluant (EP 0 382 526). The (±)-cis isomer is reacted with acetic anhydride in pyridine at room temperature to give the 2-acetate. Solvent is removed in vacuo at <30° C. The 2-acetate is then dissolved in CHCl$_3$ and washed with aqueous sodium bicarbonate. The separated organic layer is dried, and CHCl$_3$ is evaporated in vacuo. (±)-cis-2-Acetyloxymethyl-5-(uracil-1-yl)-1,3-oxathiolane is fluorina-ted as described above (Method A) by the method of Robins et al. Conversion of the 5-F-uracil base to the 5-F-cytosine base is carried out by preparation of the 4-(1,2,4-triazol-1-yl) derivative according to the methods of C. B. Reese, J. Chem. Soc., Perkins I, 1171, 1984 and W. L. Sung, Nucleic Acids Res. 9:6139, 1981, using 1,2,4-triazole and 2 equivalents of 4-chlorophenyldichlorophosphate in dry pyridine at ambient temperature. This conversion is followed by reaction with methanol previously saturated with ammonia at 0° C., and the 2-acetate is hydrolyzed to give (±)-cis-1-(2-(hydroxymethyl)-1,3-oxathiolan-5-yl)-5-fluorocytosine.

Pharmaceutical Formulations

In the following formulation Examples, the "Active Ingredient" is cis-1-(2-(hydroxymethyl)-1,3-oxathiolan-5-yl)-5-fluorocytosine.

EXAMPLE 2

Tablet Formulations

The following formulations A, B and C are prepared by wet granulation of the ingredients with a solution of povidone, followed by addition of magnesium stearate and compression.

|  | mg/tablet | mg/tablet |
|---|---|---|
| Formulation A | | |
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |
| Formulation B | | |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
|  | 500 | 300 |
| Formulation C | | |
| Active ingredient | 100 | |
| Lactose | 200 | |
| Starch | 50 | |
| Povidone | 5 | |
| Magnesium Stearate | 4 | |
|  | 359 | |

The following formulations, D and E, are prepared by direct compression of the admixed ingredients. The lactose in formulation E is of the direct compression type (Dairy Crest—"Zeparox").

|  | mg/tablet |
|---|---|
| Formulation D | |
| Active ingredient | 250 |
| Pregelatinized Starch NF15 | 150 |
|  | 400 |
| Formulation E | |
| Active ingredient | 250 |
| Lactose | 150 |
| Avicel | 100 |
|  | 500 |

Formulation F (Controlled Release Formulation)

The formulation is prepared by wet granulation of the ingredients (below) with a solution of povidone followed by the addition of magnesium stearate and compression.

|  | mg/tablet |
| --- | --- |
| (a) Active ingredient | 500 |
| (b) Hydroxypropylmethylcellulose (Methocel K4M Premium) | 112 |
| (c) Lactose B.P. | 53 |
| (d) Povidone B.P. | 28 |
| (e) Magnesium Stearate | 7 |
|  | 700 |

Drug release takes place over a period of about 6–8 hours and is complete after 12 hours.

EXAMPLE 3

Capsule Formulations

Formulation A

A capsule formulation is prepared by admixing the ingredients of Formulation D in Example 2 above and filling into a two-part hard gelatin capsule. Formulation B (infra) is prepared in a similar manner.

|  | mg/capsule |
| --- | --- |
| Formulation B |  |
| (a) Active ingredient | 250 |
| (b) Lactose B.P. | 143 |
| (c) Sodium Starch Glycollate | 25 |
| (d) Magnesium Stearate | 2 |
|  | 420 |
| Formulation C |  |
| (a) Active ingredient | 250 |
| (b) Macrogol 4000 B.P. | 350 |
|  | 600 |
| Formulation D |  |
| Active ingredient | 250 |
| Lecithin | 100 |
| Arachis Oil | 100 |
|  | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b and c using an extruder, followed by spheronization of the extrudate and drying. The dried pellets are then coated with controlled-release membrane (d) and filled into a two-piece, hard gelatin capsule.

|  | mg/capsule |
| --- | --- |
| (a) Active ingredient | 250 |
| (b) Microcrystalline Cellulose | 125 |
| (c) Lactose B.P. | 125 |
| (d) Ethyl Cellulose | 13 |
|  | 513 |

EXAMPLE 4

Injectable Formulation

| Formulation A | |
| --- | --- |
| Active ingredient | 0.200 g |
| Hydrochloric acid solution, 0.1 M, or Sodium hydroxide solution, 0.1 M q.s. to pH | 4.0 to 7.0 |
| Sterile water | q.s. to 10 mL |

The active ingredient is dissolved in most of the water (35° C.–40° C.) and the pH adjusted to between 4.0 and 7.0 with the hydrochloric acid or the sodium hydroxide as appropriate. The batch is then made up to volume with the water and filtered through a sterile micropore filter into a sterile 10 mL amber glass vial (type 1) and sealed with sterile closures and overseals.

| Formulation B | |
| --- | --- |
| Active ingredient | 0.125 |
| Sterile, pyrogen-free, pH 7 phosphate Buffer, | q.s. to 25 mL |

EXAMPLE 5

| Intramuscular injection | |
| --- | --- |
| Active ingredient | 0.20 g |
| Benzyl Alcohol | 0.10 g |
| Glycofurol 75 | 1.45 g |
| Benzyl Alcohol | q.s. to 3.00 mL |

The active ingredient is dissolved in the glycofurol. The benzyl alcohol is then added and dissolved, and water added to 3 mL. The mixture is then filtered through a sterile micropore filter and sealed in sterile 3 mL amber glass vials (type 1).

EXAMPLE 6

| Syrup | |
| --- | --- |
| Active ingredient | 0.25 g |
| Sorbitol Solution | 1.50 g |
| Glycerol | 2.00 g |
| Sodium Benzoate | 0.005 g |
| Flavor, Peach 17.42.316 9 | 0.0125 mL |
| Purified Water | q.s. to 5.00 mL |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

EXAMPLE 7

| Suppository | mg/suppository |
|---|---|
| Active ingredient | 250 |
| Hard Fat, B.P. (Witepsol H15 - Dynamit Nobel) | 1770 |
| | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 q of the mixture is filled into suitable, 2 mL plastic molds. The suppositories are allowed to cool to room temperature.

EXAMPLE 8

| Pessaries | mg/pessary |
|---|---|
| Active ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

EXAMPLE 9

Antiviral Activity Against Hepatitis B Virus (HBV)

The compound cis-1-(2-(hydroxymethyl)-1,3-oxathiolan-5-yl)-5-fluoro-cytosine, was tested as described below.

The human HBV producer cell line of $HepG_2$, 2.2.15, described and characterized by Sells et al., PNAS 84:1005, 1987 and J. Virol. 62:2836, 1988, has been shown to share many characteristics of the HBV chronically infected hepatocyte. It is infectious as demonstrated by the ability to cause disease in chimpanzees. This cell line was utilized in vitro to identify compounds with anti-HBV activity.

To test compounds for antiviral activity, monolayer cultures were treated with compound, 50–2001M for ten days. Supernatant media containing extracellular virion DNA (Dane particles) were harvested on days three, six and ten, treated with proteinase K (1 mg/mL) and sodium dodecyl sulfate (1%), and incubated at 50° C. for one hour. DNA was extracted with equal volumes of phenol followed by chloroform and then precipitated by ammonium acetate and propanol. The DNA precipitate was dissolved and collected on nitrocellulose using the procedure of Schleicher and Schuell (S & S, 10 Optical Ave., Keene, N.H. 03431, Publication No. 700, 1987), and treated as described by Southern, J. Mol. Biol. 98:503, 1975. Cells were harvested, and the intracellular DNA was obtained after cell lysis with guanidine isothiocyanate. The intracellular DNA was handled in the same manner as the extracellular DNA. After precipitation by ammonium acetate and propanol, the intracellular DNA precipitate was dissolved, cut by restriction endonuclease, Hind III, applied to agarose gel and then treated as described by Southern to determine the quantity of replicative intermediate forms. The antiviral effect of the compound was determined by measuring at least a 100-fold reduction of the amount of Dane particles extruded into the culture medium and a similar decrease in the intracellular replicative intermediates.

The results are given below:

| | Effect of cis-1-(2-(Hydroxymethyl)-1,3-oxathiolan-5-yl)-5-fluorocytosine on HBV Production in 2.2.15 Cell Cultures | | | | | | |
|---|---|---|---|---|---|---|---|
| Treatment | Intracellular HBV DNA* (pg/μg cell DNA) | | | HBV DNA in Culture Medium (pg/mL)[+]+ | | | |
| Compound (μM) | Integrated | Monomer- | Replicative intermediate | Day 0 | Day 3 | Day 6 | Day 10 |
| A. untreated | 1.1 | 2.0 | 81 | 58 | 67 | 93 | 77 |
| cells | 0.9 | 2.3 | 77 | 89 | 110 | 100 | 88 |
| 100 | 1.9 | 0.8 | 2 | 64 | 11 | 3 | 0 |
| | 1.5 | 1.9 | 1 | 34 | 19 | 2 | 0 |
| B. untreated | 1.5 | 1.9 | 110 | 65 | 44 | 86 | 71 |
| cells | 1.0 | 2.3 | 67 | 90 | 120 | 80 | 82 |
| 100 | 1.6 | 0.8 | 1 | 90 | 16 | 0 | 0 |
| | 1.0 | 0.7 | 1 | 74 | 10 | 0 | 0 |

*Analysis of intracellular HBV DNA (Dane particles) was 24 hours following the 10th day of treatment.
[+]+A "zero" indicates an undetectable level of HBV DNA, sensitivity cutoff was 0.1 pg/mL

I claim:

1. A method of treating an HBV infection in a human comprising administering a pharmaceutical composition containing an effective HBV infection treatment amount of a cis isomer of the compound of formula (I)

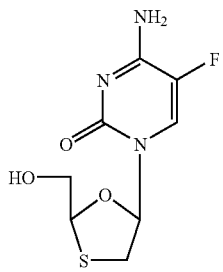

or a pharmaceutically acceptable salt thereof to said HBV infected human, wherein the composition is suitable for rectal, nasal, topical, vaginal or parenteral administration.

2. The method of claim 1 wherein the composition is suitable for rectal administration.

3. The method of claim 1 wherein the composition is suitable for nasal administration.

4. The method of claim 1 wherein the composition is suitable for topical administration.

5. The method of claim 4 wherein the administration is transdermal, buccal or sublingual.

6. The method of claim 1 wherein the composition is suitable for vaginal administration.

7. The method of claim 1 wherein the composition is suitable for parenteral administration.

8. The method of claim 7 wherein the administration is subcutaneous, intramuscular, intravenous or intradermal.

9. The method of claim 7 wherein the composition comprises an isotonic sterile injection solution.

10. A method of treating an HBV infection in a human comprising administering a pharmaceutical composition suitable for oral administration containing an effective HBV infection treatment amount of a cis isomer of the compound of formula (I)

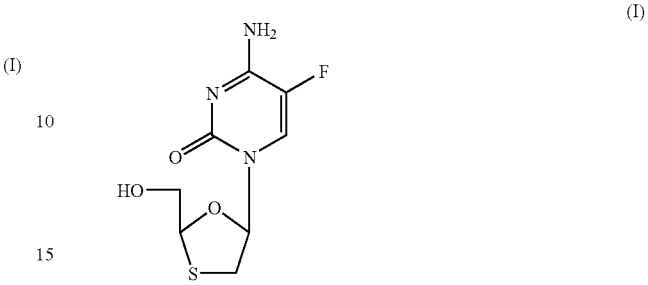

or a pharmaceutically acceptable salt thereof to said HBV infected human, wherein the composition further comprises a binder.

11. The method of claim 10 wherein the composition is in the form of a tablet.

12. The method of claim 10 wherein the binder is povidone.

13. The method of claim 10 wherein the binder is hydroxypropylmethyl cellulose.

14. The method of claim 10 wherein the composition further comprises a disintegrant.

15. The method of claim 14 wherein the disintegrant is cross-linked povidone.

16. The method of claim 14 wherein the disintegrant is cross-linked sodium carboxymethyl cellulose.

17. The method of claim 11 wherein the tablet comprises an enteric coating.

18. The method of claim 11 wherein the tablet comprises a buffering agent.

* * * * *